United States Patent
Sheng et al.

(10) Patent No.: US 12,135,201 B2
(45) Date of Patent: Nov. 5, 2024

(54) SYSTEM AND METHOD TO DETECT, ENUMERATE AND CHARACTERIZE CIRCULATING TUMOR CELLS

(71) Applicant: The Texas A&M University System, College Station, TX (US)

(72) Inventors: Jian Sheng, Corpus Christi, TX (US); Maryam Jalali-Mousavi, Woodbury, MN (US)

(73) Assignee: The Texas A&M University System, College Station, TX (US)

( * ) Notice: Subject to any disclaimer, the term of this patent is extended or adjusted under 35 U.S.C. 154(b) by 203 days.

(21) Appl. No.: 17/714,545

(22) Filed: Apr. 6, 2022

(65) Prior Publication Data

US 2022/0316864 A1      Oct. 6, 2022

Related U.S. Application Data

(60) Provisional application No. 63/171,173, filed on Apr. 6, 2021.

(51) Int. Cl.
*G01B 11/16* (2006.01)
*B01L 3/00* (2006.01)

(52) U.S. Cl.
CPC ........ *G01B 11/16* (2013.01); *B01L 3/502715* (2013.01); *B01L 2300/0663* (2013.01); *B01L 2300/168* (2013.01)

(58) Field of Classification Search
CPC ..... B01L 2200/0663; B01L 2300/0663; B01L 2300/069; B01L 3/502715; G01B 11/16; G01B 11/164; G03H 2001/005
See application file for complete search history.

(56) References Cited

FOREIGN PATENT DOCUMENTS

WO    WO-2020022252 A1 *  1/2020   ......... G01B 9/02098

OTHER PUBLICATIONS

Shaw Bagnall, Josephine, et al. "Deformability of tumor cells versus blood cells." Scientific reports 5.1 (2015): 18542 (Year: 2015).*
Varol, Rahmetullah, et al. "Holographic Cell Stiffness Mapping Using Acoustic Stimulation." arXiv preprint arXiv:2102.07480 (2021) (Year: 2015).*
Byun, Sangwon, et al. "Characterizing deformability and surface friction of cancer cells." Proceedings of the National Academy of Sciences 110.19 (2013): 7580-7585 (Year: 2013).*

* cited by examiner

*Primary Examiner* — Tarifur R Chowdhury
*Assistant Examiner* — Roberto Fabian, Jr.
(74) *Attorney, Agent, or Firm* — Winstead PC

(57) ABSTRACT

In an embodiment, the present disclosure pertains to a method of performing circulating tumor cell (CTC) analysis. In general, the method includes flowing a sample through a CTC microfluidic platform, deforming a CTC within the sample, measuring CTC deformation through an imprint of the deformed CTC, processing data related to the measuring, and at least one of identifying or characterizing parameters related to the data that enables at least one of detection of CTCs, enumeration of CTCs in the sample, characterization of biophysical properties, CTC cell size, CTC cell membrane deformability, stresses on CTC cell membranes, adhesion stress on CTC cells, normal stress of CTC cells, or combinations thereof. In some embodiments, the flowing includes passing the sample through at least one channel of the CTC microfluidic platform having a constricted section.

19 Claims, 7 Drawing Sheets

SYSTEM AND METHOD TO DETECT, ENUMERATE AND CHARACTERIZE CIRCULATING TUMOR CELLS

CROSS-REFERENCE TO RELATED APPLICATIONS

This patent application claims priority from, and incorporates by reference the entire disclosure of, U.S. Provisional Application 63/171,173 filed on Apr. 6, 2021.

STATEMENT REGARDING FEDERALLY SPONSORED RESEARCH

This invention was made with government support under W911NF-17-1-0371 awarded by the Army Research Office. The government has certain rights in the invention.

TECHNICAL FIELD

The present disclosure relates generally to detecting and characterizing circulating tumor cells (CTCs) and more particularly, but not by way of limitation, to detection, enumeration, and characterization of CTCs in whole blood.

BACKGROUND

This section provides background information to facilitate a better understanding of the various aspects of the disclosure. It should be understood that the statements in this section of this document are to be read in this light, and not as admissions of prior art.

Circulating cancer cells (CTCs) are cancer cells detached from a primary or secondary tumor and enter the blood stream. CTCs are ideal biomarkers in patient prognosis and treatment monitoring since they are responsible for the development of metastasis. The major obstacle to detect and isolate CTCs is the scarcity of these cells in the blood stream (1 to 10 CTCs per mL in the whole blood of cancer patients). Thus, the challenge, and also urgent demand, is to develop a technology that can process large volumes of blood in a short time and nondestructively detect in a manner that is independent of molecular signatures. The existing methods for detection and isolation of CTCs are: (1) nucleic acid-based methods for CTC detection; (2) physical properties-based methods for CTC isolation, for example, isolation of CTCs based on size and mechanical plasticity (e.g., electrokinetic isolation of CTCs); and (3) antibody-based methods for CTC detection and isolation, for example, immunocytochemistry (ICC) methods for CTC detection, immunomagnetic methods for CTC isolation, and adhesion-based methods for CTC isolation. The shortcoming of nucleic acid-based methods for CTC detection is that they can only resolve whether a sample is positive for one or more markers. Physical properties-based methods all suffer from various practical issues including, but not limited to, clogging, low capture efficiency, and are ineffective to detect heterogeneous CTCs in whole blood, under which circumstances their capabilities and clinical relevance are yet to be substantiated. Antibody-based methods for CTC detection methods inherently introduce a positive bias on CTC selection but fail to recognize cells that lack biomarkers and are incapable of resolving the heterogeneous subpopulations of CTCs (e.g., mesenchymal phenotype). Additionally, complicated processes and high cost of affinity ligands have hindered their clinical applications.

The development of this invention was funded in part by the Cancer Prevention and Research Initiative of Texas under grant number RP200593.

SUMMARY OF THE INVENTION

This summary is provided to introduce a selection of concepts that are further described below in the Detailed Description. This summary is not intended to identify key or essential features of the claimed subject matter, nor is it to be used as an aid in limiting the scope of the claimed subject matter.

In an embodiment, the present disclosure pertains to a method of performing circulating tumor cell (CTC) analysis. In general, the method includes flowing a sample through a CTC microfluidic platform, deforming a CTC within the sample, measuring CTC deformation through an imprint of the deformed CTC, processing data related to the measuring, and at least one of identifying or characterizing parameters related to the data that enables at least one of detection of CTCs, enumeration of CTCs in the sample, characterization of biophysical properties, CTC cell size, CTC cell membrane deformability, stresses on CTC cell membranes, adhesion stress on CTC cells, normal stress of CTC cells, or combinations thereof. In some embodiments, the flowing includes passing the sample through at least one channel of the CTC microfluidic platform having a constricted section.

BRIEF DESCRIPTION OF THE DRAWINGS

A more complete understanding of the subject matter of the present disclosure may be obtained by reference to the following Detailed Description when taken in conjunction with the accompanying Drawings wherein.

DETAILED DESCRIPTION

Figure 1A:
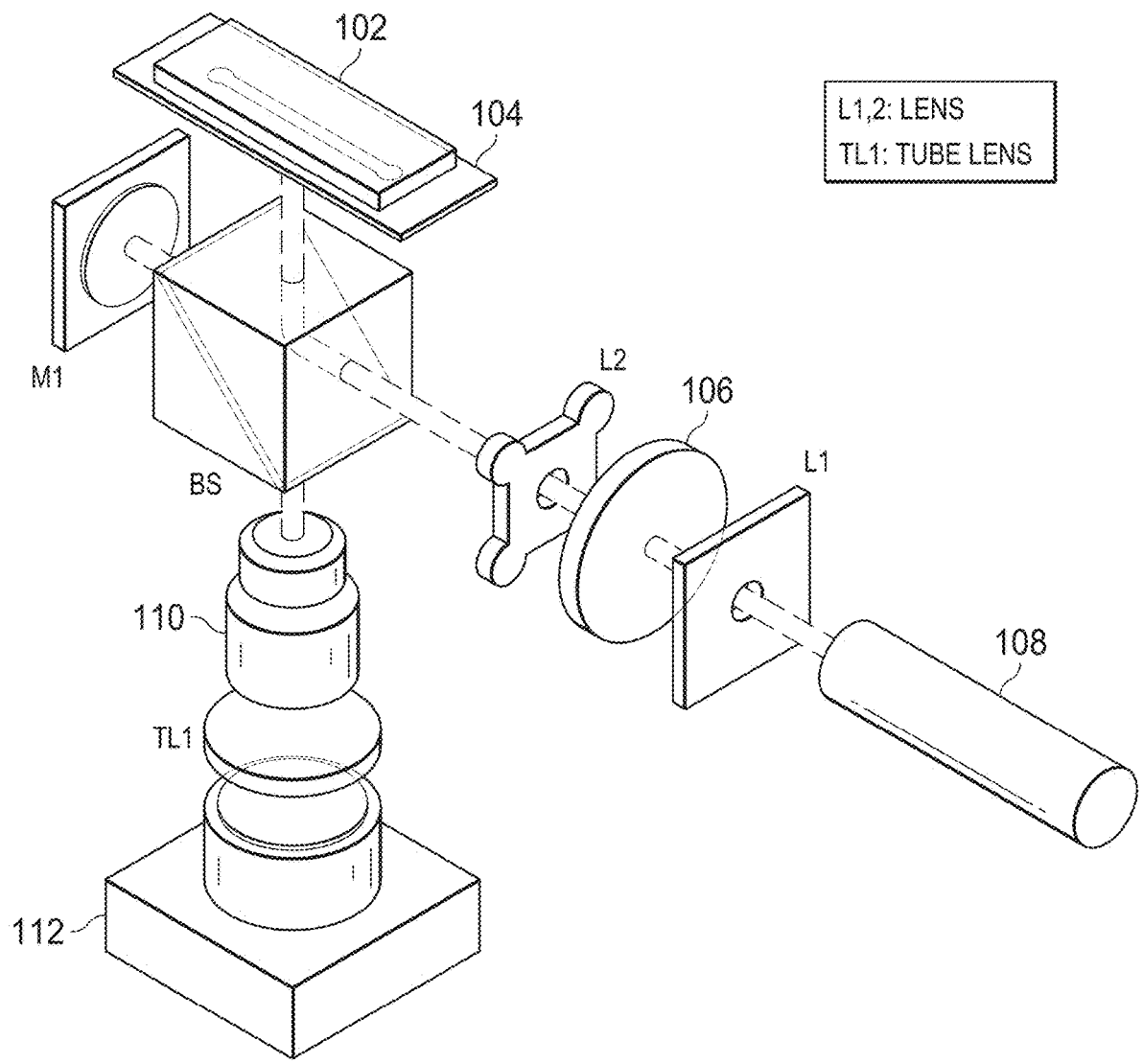
FIG. 1A illustrates a reflection digital holographic microscopic interferometer schematic according to aspects of the present disclosure.

It is to be understood that the following disclosure provides many different embodiments, or examples, for implementing different features of various embodiments. Specific examples of components and arrangements are described below to simplify the disclosure. These are, of course, merely examples and are not intended to be limiting. The section headings used herein are for organizational purposes and are not to be construed as limiting the subject matter described.

In various embodiments, the present disclosure pertains to a paradigm-shifting cancer detection technology that includes, for example, new cancer diagnostic systems, devices, and measurement methodologies, and their integration, that allows high throughput circulating tumor cell (CTC) detection, enumeration, and simultaneous biomechanics characterizations, including, but not limited to, cell size, deformability, and membrane viscoelasticity of CTCs in a patient's whole blood without any chemical and mechanical modifications. The CTC detection systems disclosed herein includes a thin film "tactile" detection and characterization microfluidic device, whole blood sample handling sub-system, optical non-intrusive nanostrain (nanometer scale strain deformation) measurement sensor readout/subsystem (e.g., digital holographic microscopic interferometry; DHMI), and data analysis subsystem.

The disclosed thin film "tactile" microfluidic subsystem is a new technology composed of a nm-thick wrinkle-free metallic thin film in polymer (WiMTiP) nanostrain ("tactile") sensor combined with a DHMI that is virtually applicable to all metastatic cancers and resolves the throughput challenges described in brief above. WiMTiP-DHMI platforms have the potential to enumerate CTCs in whole blood sample, and simultaneously characterize mechanical properties including, but not limited to, cell size, membrane stiffness, and surface forces (e.g., adhesion and pressure) without destruction or modification to the sample, which may be reserved for other hemolytic analysis. In some embodiments, the WiMTiP-DHMI platforms have the potential to enumerate CTCs in chemically tampered samples, samples less than whole blood cells, prostate cells PC3 or LNCap, breast cancer cells MCF-7, MB231, T47D, 4T1, or MDA-MB-231, lung cancer cells A549 or H358, plasma, red blood cells, white blood cells, a phosphate buffered saline (PBS)-blood mixture, and combinations thereof.

As described above, the present disclosure pertains to new paradigm-shifting cancer detection developments that include cancer detection methodologies, WiMTiP detection and characterization devices, data analysis software, and their integration to allow high throughput CTC detection, enumeration, and simultaneous biomechanics characterizations including, but not limited to, cell size, deformability, and membrane viscoelasticity of CTCs in a patient's whole blood without any chemical and mechanical modifications. More specifically, in particular embodiments, the present disclosure relates to methods of CTC detection, enumeration and characterization, and WiMTiP-DHMI CTC detection/characterization systems.

Differing from existing methods for CTC detection and characterization, such as, for example, nucleic acid-based, physical properties-based methods (e.g., isolation based on CTC cell size, mechanical plasticity, and electrokinetic properties), and antibody-based detection and isolation methods (e.g., immunocytochemistry detection, immunomagnetic-labeling, and adhesion-based methods for CTC isolation), the present disclosure utilizes a new "tactile" microfluidic technology that detects, enumerates, and characterizes CTCs in a patient's whole blood non-intrusively and optically by quantifying the mechanical properties (e.g., membrane stiffness and viscoelasticity) of cells in a whole blood sample. Differing in detection paradigms, the present disclosure exploits the substantial differences in membrane characteristics of CTCs (softer and highly deformable) to that of other blood cells (comparably stiffer). This difference in membrane stiffness is further amplified by forcing cells through a constriction with a cross-sectional height comparable to a CTC cell but considerably larger than other blood cells. As CTCs squeeze through the constriction, they deform and exert a large force that causes reciprocal wall deformations, while other hemocytes deform less and impose consequently no, or much smaller, deformations. These cell-induced wall deformations are measured by a nanostrain ("tactile") sensor at a sensitivity of ~1.5 pN/nm and are optically readout by a holographic interferometer at a resolution of 10 nm. This capability is enabled by a polymer-metal metamaterial, such as, for example, WiMTiP fabrication technology and DHMI.

In various aspects of the present disclosure, the WiMTiP-DHMI system includes a blood handling subsystem having a pump (e.g., syringe or peristaltic), sterilized tubes and fittings, and a WiMTiP "tactile" sensor microfluidic channel that is capable of registering cell-induced nanometer deformations, as well as a DHMI subsystem including a holographic optical interferometer and associated data analysis algorithms capable of deciphering holographic interferograms to reconstruct three-dimensional (3D) nanometer CTC-induced strain deformation.

In one embodiment, the WiMTiP microfluidic channel includes a top-half straight channel containing a long mid-section with a smaller channel height (e.g., ~15 μm, slightly smaller than a CTC but larger than other hemocytes) made of polydimethylsiloxane (PDMS). In some embodiments, the WiMTiP microfluidic includes more than one channel such as, for example, three channels. In some embodiments, the WiMTiP microfluidic includes at least one channel. The bottom section of the device includes glass covered by a WiMTiP nanostrain sensor (e.g., layers from the glass: 1.5 mm PDMS, 100 nm aluminum patterned thin-film sensor, and 25 μm PDMS). The bottom section of the microfluidic channel is the very first nanostrain sensor made possible using WiMTiP technology. This thin film device is optically smooth (i.e., highly reflective) and highly electrically conductive. Previously, in similar metal-polymer materials, a metal film was located on top of a compliant polymer substrate. In aspects of the present disclosure, a metal layer is sandwiched between two polymeric layers. This allows the sandwiched thin film to inhere elasticity from bulk polymers and prevent it from delaminating and cracking. Furthermore, in similar metal-polymer materials the metal film was wrinkled (i.e., glossy) and/or pre-stressed (e.g., loaded). However, in aspects of the present disclosure, the sandwiched metal film is wrinkle-free and has no-residual stress. Moreover, in various aspects of the present disclosure, the metal thin film is optically smooth (i.e., specular reflectivity) and electrically conductive. In contrast, previously the film was optically rough (i.e., diffusive reflectivity) and electrically conductive. In addition, according to aspects of the present disclosure, the technique to fabricate the multi-layer polymer metal composite is simple, scalable, and applicable to different metal and polymer pairs in comparison to those techniques that were previously available.

The reflective DHMI is composed of a laser and beam shaping optics, as well as a reflective Mach-Zehnder interferometer including a beam splitter, mirror in reference beam, thin film mirrors in WiMTiP sensors, and a recording camera. During measurement, the collimated beam (BM1) is split by a beamsplitter (BS1) into reference (BM2) and object (BM3) beams. The redirected object beam by the "deformed" micro mirrors in WiMTiPs is combined with the reference beam redirected by mirror (M1) to produce interference fringes. An imaging lens is introduced after the beamsplitter to project the interference fringes at its imaging plane onto the camera. It should be noted that the imaging plane of the lens is placed squarely at the resting plane of the WiMTiP sensor. The nano-scale deformation of the flexible mirror in WiMTiP is registered as its deviation, $\delta_z(x, y)$ in the depth (z) direction from its rest position, $z_0(x, y)$, to the glass substrate (or $\delta_z=z-z_0$). The deviation subsequently introduces a phase change into the object beam, $U_o(x, y)=A_o \exp[(j2kn_p \cdot (z_0-\delta_z)]$, where A is the amplitude, $k=2\pi/\lambda$ is the wave number, and $n_p$ is the index refraction of elastomer, illuminating from the bottom onto the deforming micromirror. The reflected object beam combined with reference beam, $U_r(x, y)=A_r\exp(j2kn_p \cdot z_0)$, forms the interference pattern, $I(x, y)=A_o^2+A_r^2+2A_rA_o \cdot \cos(j2n_p k\delta_z)$. The phase information recorded in I(x, y) is then recovered (or reconstructed).

Figure 1B:
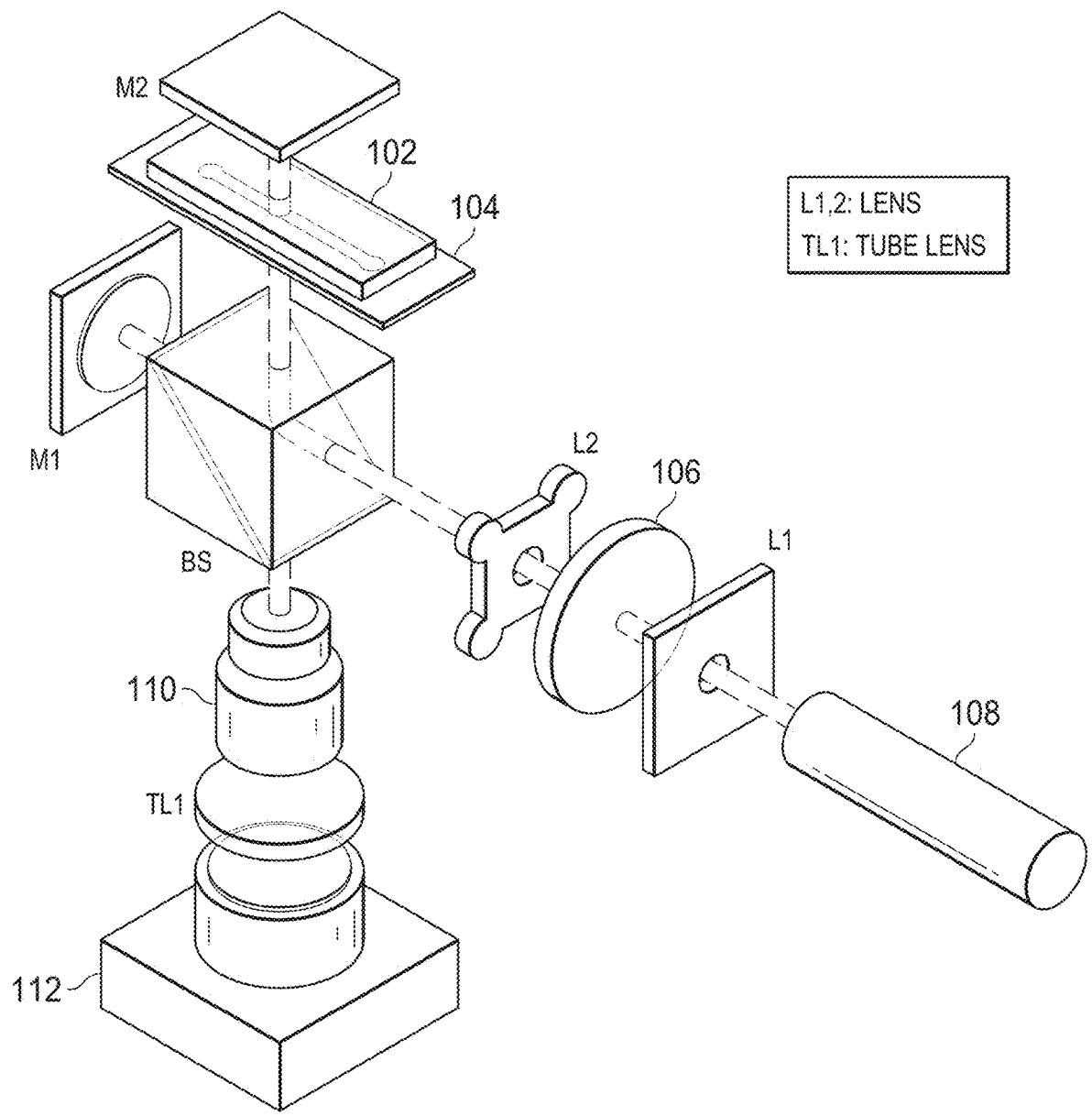
FIG. 1B illustrates a transmission digital holographic microscopic interferometer schematic according to aspects of the present disclosure.

FIG. 1A shows a reflection digital holographic microscopic interferometer schematic according to aspects of the present disclosure. FIG. 1B shows a transmission digital holographic microscopic interferometer schematic according to aspects of the present disclosure. In the examples shown in FIG. 1A and FIG. 1B, both commonly include a CTC microfluidic 102, a WiMTiPiT sensor 104, a pinhole 106, a laser 108 (continuous wave (CW) He—Ne laser; λ=632.5 nm), an objective 110, and a camera 112. In some embodiments, various setups of the present disclosure utilize a reflective DHMI which includes a 25 mW CW He—Ne laser (λ=632 nm) spatially filtered by an objective L1, a 25 µm pinhole 106 and collimated to a 50 mm Gaussian beam by a collimating lens L2. A 2" 50/50 beamsplitter (BS) splits the illumination equally into a reference and object beam, both of which, after being redirected by a 3" mirror and micro-mirror in WiMTiP, respectively, is recombined by the same BS and redirected by a 3" right-angle prism to generate interference fringes. The interference fringes are recorded by a microscope including an infinity corrected objective 110, tube lens TL1, and a large format camera 112. To resolve 3D deformation within a WiMTiP sensor adequately, a large number of fringes must be resolved with magnifications (e.g., 5×, 10×, or even 40×). Although a microscope objective is used as an imaging lens, the short working distance (WD) of an objective prevents the insertion of any other necessary optics (e.g., BS and prism). The techniques of the present disclosure circumvent this problem by using a macro imaging lens with the zoom (Nikon Nikor 105, minimum WD=6") as a projection lens that transfers the interferences formed at the plane of flexible mirror in WiMTiP to the image plane of the lens downstream where an infinity corrected microscope is located. The imaging system, including microscope and imaging lens, has a WD>6" and a resolution of 10,000 lines/mm at 10× magnification. In some embodiments, various setups of the present disclosure utilize a transmissive DHMI which includes a laser spatially filtered by an objective (L1), a 25 µm pinhole 106 and collimated to a 50 mm Gaussian beam by collimating lens (L2). A 2" 10/90 beamsplitter (BS) splits the illumination into a reference (10%) and object beam (90%). The object beam passing through CTC microfluidics with WiMTiP sensor of 30% transmissivity is redirected by mirror M2 back towards the fluidics. After the reference beam being redirected by a 3" mirror M1, both beams are recombined by the same BS to generate interference fringes. The interference fringes are recorded by a microscope including an infinity corrected objective 110, tube lens TL1, and a large format camera 112. In some embodiments, various setups of the present disclosure utilize a coherent light source, including continuous wavelength (CW) laser, pulsed laser, diode pumped solid state (DPSS) laser, and laser diode, at various emission wavelength (λ) ranging from 375 nm to 1064 nm.

In some embodiments, other coherent sources including pulsed lasers, continuous wavelength (CW) lasers, diode pumped solid state lasers, and laser diodes, whose emission wavelength covers the entire visible spectrum (i.e., ultraviolet to near infrared) are utilized. Pinhole sizes can include, without limitation, 5 µm, 10 µm, 20 µm, 25 µm, or other similar size. In some embodiments, the beamsplitter can be a polarized beamsplitter or a broadband beamsplitter.

Additionally, the present disclosure pertains to various aspects, such as, without limitation, fabrication methods of WiMTiP CTC microfluidics, digital readout/reconstruction methods of cell-induced WiMTiP sensor deformations, and CTC cell detection and characterization methods and processes.

As existing fabrication methods provide limitations, such as, for example, restriction caused by ring size (e.g., PDMS metallization methods where PDMS is confined within an aluminum (Al) ring) and small coverage areas (e.g., pattern transfer methods via a poly(acrylic acid) sacrificial layer for PDMS metallization and pattern transfer method where gold (Au) patterns are embedded in a PDMS sheet), various embodiments of the present disclosure pertain to enhanced fabrication methods. With respect to the fabrication of WiMTiP CTC microfluidics, the fabrication involving different microfabrication processes such as soft lithography, physical vapor deposition, sputtering with shadow masks, and plasma surface activation, wet etching, is generally described in the following sequences: (1a) The fabrication of the top half of the device is started by utilizing AUTOCAD® to draw the shape of the straight channel containing a long midsection. The AUTOCAD® drawing of the channel is then printed on thin polymer transparency film at 10,000 dpi (2.5 µm), or a laser quartz photomask print in chromium deposited on the quartz at 420,000 dpi (600 nm). An SU8 mask over the glass is patterned and formed using photolithography, and wet-etching of the SU8 patterned glass substrate is conducted by alternatively etching by HF and HCl until the channel reaches its designated height (e.g., 12 µm). The inlet and outlet ports are then drilled after etching; (1b) The bottom-half of the microchannel is then fabricated layer-by-layer by first mixing SYLGARD™ 184 with a curing agent at about a 10:1 ratio. After degassing, the mixture is poured on a pre-cleaned glass slide, and then cured at 65° C. for 48 hours. A nanometer-thick (e.g., >200 nm) Perylene-C jammer is deposited on the cured PDMS. Nanometer-thick (e.g., 50 nm) aluminum is sputtered on the substrate, during which a shadow mask is applied to generate the shape of WiMTiP sensor. Finally, a micron-thick (e.g., 25 µm) PDMS layer is spincoated and cured at 65° C. for 48 hours. Additional Perylene-C can be deposited before the top PDMS layer to prevent leaching of sensory materials in liquid; and (1c) The integration of the top and bottom microchannel is achieved by, for example, 02-plasma bonding.

Figure 2:
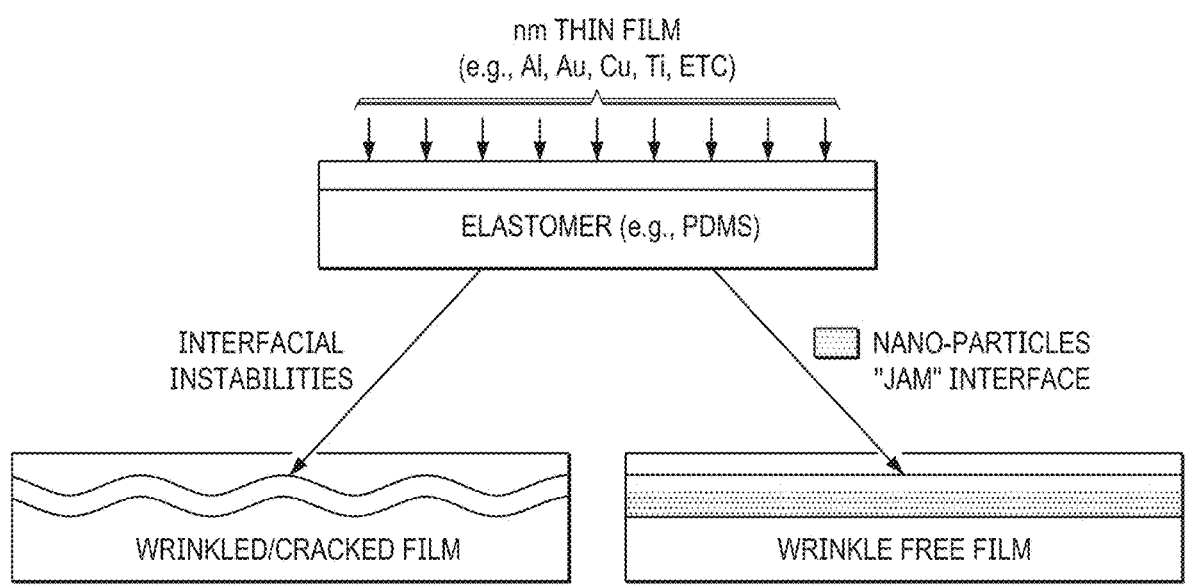
FIG. 2 illustrates that deposition of a nanoparticle jammer layer onto a compliant substrate prior to metal deposition suppresses the interfacial instability and prevents thin film buckling and wrinkle formation.
Figure 3:
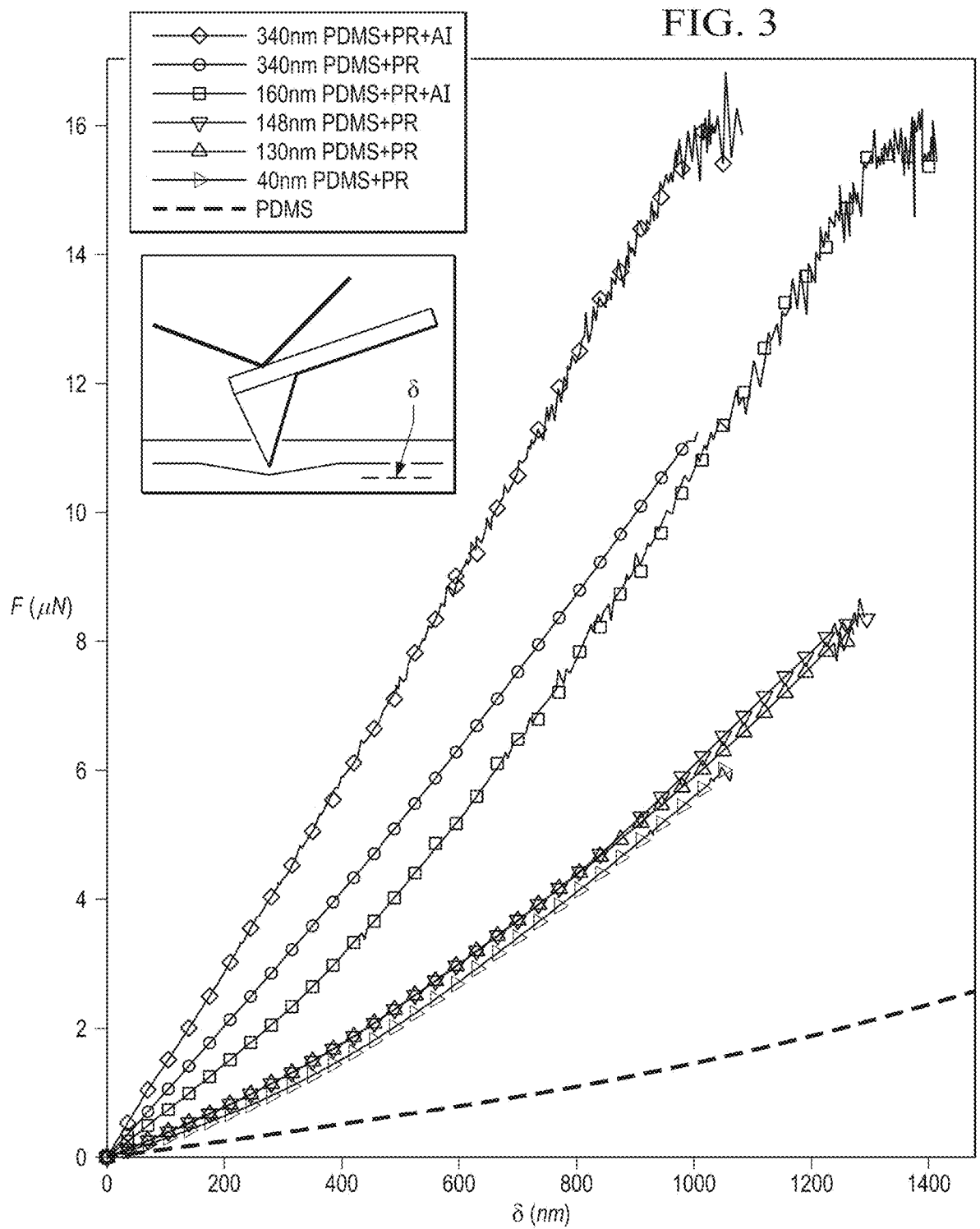
FIG. 3 illustrates that as the thickness of the jammer increases beyond ~150 nm, a wrinkle free metallic thin film in polymer (WiMTiP) becomes increasingly elastic (linear $F$–$\delta$).

Deposition of a nanoparticle jammer layer onto a compliant substrate prior to metal deposition suppresses the interfacial instability and prevents thin film buckling and wrinkle formation. An illustrative example of this is shown in FIG. 2. The nanoparticle jammer suppresses interfacial instability by changing local material properties. FIG. 3 shows that as the thickness of the jammer (e.g., Parylene-C or PR) increases beyond ~150 nm, a WiMTiP becomes increasingly elastic (linear F–δ). The enhanced viscoelasticity of WiMTiP allows it to register strains (normal and shear). As illustrated in FIG. 3, the F–δ curves are parabolic when t<150 nm. Furthermore, encasing the metal thin film in the polymer matrix enhances the elasticity of the film.

With respect to the readout and reconstruction methods for measuring CTC-induced WiMTiP sensor deformation, digital holographic interferograms are recorded by a high-speed camera and streamed into a cloud-based GPU system. The data stream is processed through fringe enhancement using correlations, omni-direction phase field reconstructions with de-warping, 3D deformation reconstruction algorithm processing, and subsequently a model for CTC-induced WiMTiP deformation if formed. In some embodiments, various forms of data analysis hardware can include, without limitation, cloud-based GPU systems, server-based edge computing systems, or dedicated high-performance clusters (HPCs).

In addition, numerous advantages and applications exist for various embodiments of the present disclosure. For example, systems disclosed herein utilize a thin film "tactile" microfluidic platform, which as described above, is a new technology utilizing a nanometer-thick WiMTiP nanostrain ("tactile") sensor and a DHMI that is virtually applicable to all metastatic cancers and resolves the throughput challenges of previous systems. In addition, the systems and methods of the present disclosure allow for applicability to all metastatic cancers. The systems and methods to enumerate CTCs disclosed herein are based on simultaneously measuring multiple biophysical properties of metastatic and non-metastatic cancer cells. Such a label-free approach may allow for CTC detection in all metastatic and non-metastatic cancers. Furthermore, the systems and methods of the present disclosure provide robust CTC counts. In comparison to existing slow processing speeds at typically 1 mL/hour, the systems and methods presented herein offer significant throughput (~7 mL/min) and robust CTC counts. Moreover, greater phenotyping the heterogeneity in CTCs with multiple biophysical properties are also made possible. The approaches disclosed herein are culture-free and provide multiple readouts significantly resolving the heterogeneity in CTCs. The multiple biophysical "fingerprinting" and subsequent classification enable phenotyping CTCs in its natural complexity.

Various aspects of the present disclosure provide for a WiMTiP-DHMI platform that provides a stable and reliable platform to investigate the presence of CTCs in whole blood, as well as the exact size and shape of the cells. The devices disclosed herein are capable of being utilized to monitor the deformation of the cells during the course of the disease. These devices provide a superior alternative to existing methods as non-invasive techniques for determining the state of the metastasis or the overall progression by measuring the mechanical characteristics of cell membrane, such as membrane stiffness, topography, mechanical stresses, and the like. The WiMTiP-DHMI platforms disclosed herein provide point-of-care blood analysis and CTC identification and "fingerprinting" for early cancer detection in addition to monitoring prognosis.

In general, enumeration of CTCs using micro/nanofluidic technology fall under two broad categories: (1) affinity-based technologies through molecular recognition, which use affinity ligands including antibodies and aptamers to target biomarkers on the cell surface; and (2) physical-based isolation using cells physical properties to distinct CTCs from background hemocytes. Affinity-based methods inherently introduce a positive bias on CTC selection, but fail to recognize cells that lack biomarkers and are incapable of resolving the heterogeneous subpopulations of CTCs (e.g., mesenchymal phenotype). Additionally, complicated processes and high cost of affinity ligands have hindered their clinical applications. Physical-based methods utilize differences in physical properties (e.g., size, deformability, density, hydrodynamics, and dielectric properties) of CTCs to those of hemocytes. However, many suffer from various practical issues including clogging, low capture efficiency, and ineffective to detect heterogeneous CTCs in whole blood, under which circumstances their capabilities and clinical relevance are yet to be substantiated.

Detection robustness and throughput of operations are major limitations of existing methods. Techniques based on affinity ligands provide high selectivity, but are ineffective in dealing with CTCs heterogeneity due to lacking generic biomarkers, whereas diversities in physical properties of CTCs overlap with those of hemocytes. Throughput is another technical bottleneck, as typical processing speeds are ~1 mL/h for fluidic-based methods (e.g., CTC-chip and HB-chip), and recently ~1 mL/min for single pass yet suffer from low detection efficiency (e.g., vortex chip and deterministic lateral displacement chip). These limitations arise because large flow rates through confined passage affect the efficiency of capture and damage CTCs by shear. Non-microfluidic commercial methods (e.g., CELLSEARCH® and MagSweeper) handle much larger volumes, but involve significant steps (e.g., washing, centrifugation, and labeling). Currently, CTC enumeration of a blood sample takes more than 12 hours, which necessitates the storage of the samples potentially affecting CTC counts and molecular expression. Additionally, all prior techniques require the modifications of patients' blood samples, such as lsying hemocytes, chemical labeling, and cell surface modification with chemicals, probes, and capturing/isolating CTCs from the blood.

As previously mentioned, existing technologies offering CTC detection have many shortcomings, for example, the lack of sensitivity to one or more markers and not allowing for direct enumeration and cytomorphological study of CTCs, the lack of proper representation of the morphologically heterogenous nature of the cancer cells, obstacles arising from lack of a surface maker that is strongly articulated by all CTCs, and complicated processes with high cost of affinity ligands. The WiMTiP-DHMI systems and methods of the present disclosure address these limitations. For example, the systems and methods disclosed herein provide high-throughput for CTC cell detection and enumeration in whole blood (i.e., no tampering of patient blood sample). The WiMTiP-DHMI is capable of processing 10 mL of whole blood in a shorter time (~2 min) compared to other existing techniques. Furthermore, the high sensitivity of the systems and methods disclosed herein allow for simultaneous and non-intrusive characterization of CTC mechanical properties including cell size, deformability, and viscoelasticity of CTCs, which enables the "fingerprintings/distinguishing" of the origin of CTC cells. Additionally, as disclosed herein, sample preparation and handling does not require physical, chemical, and/or biological modification. This allows further analysis of patients' blood sample for conventional blood analysis and provides more comfort to the patient during screening.

WORKING EXAMPLES

Reference will now be made to particular embodiments of the present disclosure and data that provides support for such embodiments. However, it should be noted that the disclosure below is for illustrative purposes only and is not intended to limit the scope of the claimed subject matter in any way.

CTCs in blood are recognized to be the primary drivers of metastasis in cancer and considered as an important biomarker in patient prognosis as well as monitoring treatment. Despite growing interests and rapid advancements in micro/nanofluidic technologies to isolate, detect, enumerate and subsequently characterize CTCs from the patients' whole blood, progress in CTC-related research has been complicated by their extremely low counts in peripheral blood (1-10 CTC in $10^9$ blood cells), highly heterogeneous morphologies, and highly entangled tumor-dependent molecular expression profiles. Thus, the challenge, and also urgent demand, is to develop a technology that can process large volumes of blood in a short time and non-destructively detect in a manner that is insensitive to tumor-dependent molecular signatures. Embodiments of the present disclosure seek to demonstrate new technology with a focus on high throughput and nondestructive CTC detection, enumeration, and simultaneous biophysical characterizations including, for example, cell size and deformability.

As previously discussed, detection and enumeration of CTCs using micro/nanofluidic technology fall under two broad categories: (1) affinity-based technologies through molecular recognition, which use affinity ligands including antibodies and aptamers to target biomarkers on the cell surface, and (2) physical based detection and isolation using cells physical properties to distinct CTCs from millions of background hemocytes. Affinity-based methods inherently introduce a positive bias on selection of CTCs. However, they often fail to recognize cells that lack biomarkers and consequently in capable of resolving the heterogeneous subpopulations of CTCs (e.g., mesenchymal phenotype). Additionally, the complicated production process, strict preservation conditions and high cost of affinity ligands have severely hindered their wide applications in reality. Physical based methods utilize the difference in physical properties (e.g., size, deformability, density, hydrodynamics, and dielectric properties) of CTCs to those of hemocytes. However, many of them suffer from various practical issues including being prone to clogging, low detection efficiency, and ineffective to detect heterogenous CTCs in whole blood, under which circumstances their capabilities and clinical relevance are yet to be substantiated.

Robustness in underlying principles and throughput of operations are major limitations of all existing methods. Techniques based on affinity ligands targeting the surficial biomarkers of CTCs provides high selectivity but often ineffective in dealing with CTCs heterogeneity due to lacking generic biomarkers, whereas the distributions of physical properties of CTCs are often widely spread and overlapped with those of hemocytes. Throughput is another technical bottleneck on the applications of all existing methods. Typical processing speeds are about 1 mL of blood per hour for microfluidic-based methods (e.g., CTC-chip or HB-chip), and recent studies have reported shorter single pass processing time at ~1 mL/min (e.g., vortex chip or deterministic lateral displacement), but with low efficiency. Since there are only 1-10 CTCs per mL, multiple devices or single device operating through multiple passes resulting in several hours processing are needed to achieve reliable counts. These limitations arise because increasing injection flow rates affect efficiency of capture and damage CTCs by shear. Non-microfluidic commercial methods (e.g., CELL-SEARCH® or MAGSWEEPER™) handle much larger volumes, but they involve significant and costly sample preparation and processing steps (e.g., washing, centrifugation, and labeling). Currently, it is not uncommon to take a half day to analyze a patient blood sample, which necessitates storage of blood samples, potentially affecting CTC counts and molecular expression.

As such, the present disclosure seeks to develop nanostress microfluidic platforms, a new technology composed of a nanometer thick WiMTiP flexible nanostrain ("tactile") sensor and a DHMI that is applicable to virtually all metastatic cancers and resolves current throughput challenges in enumerating and simultaneously characterizing mechanical properties of CTCs in whole blood sample. As discussed below, the microfluidic WiMTiP-DHMI platform (shown in FIG. 4) has the potential capability to detect, enumerate CTCs in a whole blood sample, and simultaneously quantify key biophysical properties, such as cell size, membrane deformability, stresses on cell membrane (e.g., adhesion and normal stress), without destruction or modification to the sample that would preserve for other downstream analysis and culturing. Owing to its simple sample handling, the WiMTiP-DHMI platform is potentially capable to process 10 mL of whole blood in under 12 min including time for sample preparation, running experiment, data collection and analysis. Such throughput surpasses all existing CTC enumeration technologies by orders of magnitude.

Differing from existing methods, the disclosed technology is based on the following principles: (1) the membrane of a CTC is significantly soft and elastic (i.e., highly deformable) in comparison to that of other hemocytes. As a CTC squeezes through a confined passage with comparable cross-sectional dimensions (e.g., 20 μm in height) to CTC diameter (e.g., 13-25 μm), it deforms and exerts significant stresses on cell membrane, which also leaves a larger "tactile footprint" (or cell-induced wall deformation) on the passage wall that may be measured directly by a sensitive strain sensor sensitive. It should be noted that such a cell-induced deformation is only tens of nanometers for most materials; (2) as a suspension (e.g., whole blood) containing colloids of various sizes (e.g., white blood cells (WBC), red blood cells (RBC), platelets, CTC, etc.) passes through a confinement, bulk biomechanical properties exhibit a strong scale decency on local colloidal composition. For example, a CTC in a confinement with comparable size is "felt" via pressure like a discreet cell and dominates bulk mechanical properties like elasticity and viscosity, while an RBC (e.g., 5-9 μm) contributes to those properties as a fraction of the continuum; and (3) cell-induced wall deformation is significantly amplified by interacting with a compliant surface at resonance frequency and "tactile" signature propagates as an elastic sound wave, which will allow rapid sensing remotely. The above considerations inspired the methods and systems disclosed herein.

Figure 4:
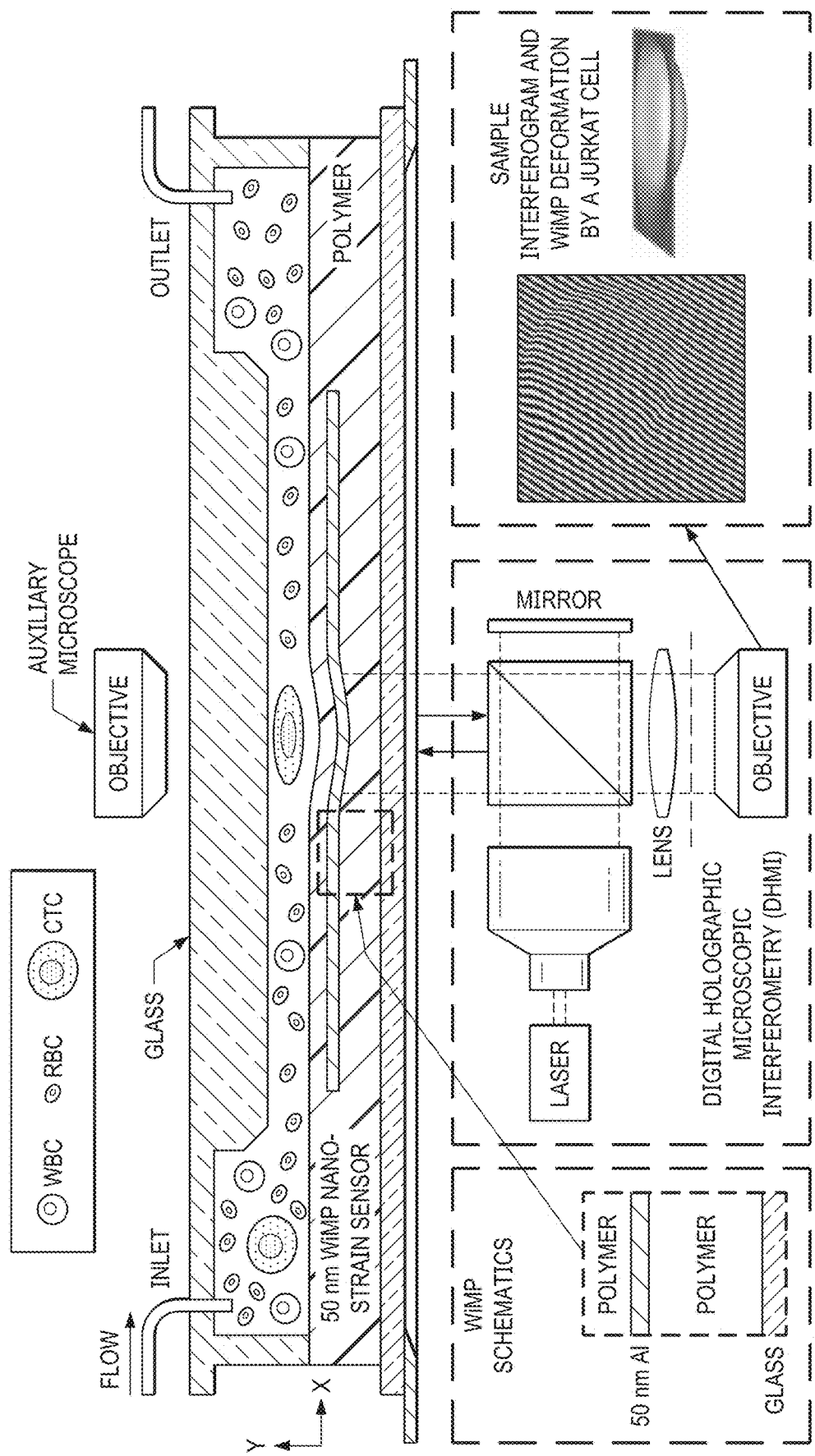
FIG. 4 illustrates schematics of the detection and mechanical characterization of circulating tumor cells (CTC) using a WiMTiP nanostrain sensor and digital holographic interferometry according to aspects of the present disclosure.

The detection principle and the generic device are graphically elucidated in FIG. 4, a system has been constructed and tested in a laboratory. Briefly, the WiMTiP-DHMI platform includes a glass microfluidic channel containing a 50 nm WiMTiP (i.e., wrinkle free metallic thin film in polymer) strain sensor and a DHMI capable of measuring 10 nm deformation (a very conservative estimation) remotely. Shown in FIG. 4, a top-half straight channel contains a constricting section with a reduced cross-section (e.g., ~15 μm, slightly smaller than a CTC but larger than other hemocytes). A polymeric bottom layer embedded with a 50 nm thick wrinkle free Al thin film (FIG. 4) is covalently bonded with the top channel to form the microfluidic device. A component of a WiMTiP is the nm wrinkle-free metallic thin film. Being wrinkle-free (i.e., smooth and no residue stress), the WiMTiP is highly reflective and deformable (i.e., a flexible nano mirror). As the whole blood passing through the constricted section of the microchannel, CTCs deform greatly and cause a reciprocal indentation on the soft polymer wall, whilst other hemocytes leave much a smaller "tactile imprint". Such an imprint "marked" by the WiMTiP film and registered as a phase modulation onto the collimated coherent illumination are recorded and measured directly by a DHMI. Through further modeling, the deformation of WiMTiP to cell-induced wall stresses are related and subsequently mechanical properties of CTCs are approximated. Results of wall deformation by a passing leukemia cell (Jurkat) is shown in FIG. 4.

Figure 5A:
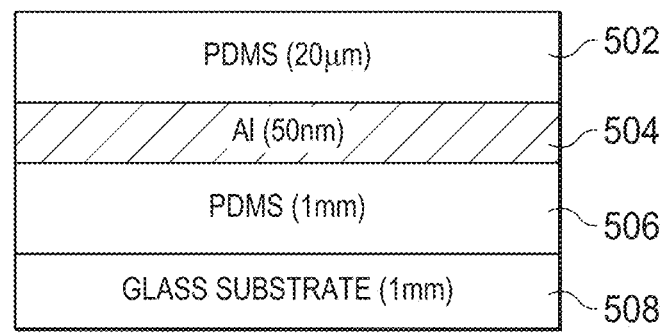
FIG. 5A illustrates a polydimethylsiloxane (PDMS)-Al WiMTiP schematic and sample according to aspects of the present disclosure.

Although the abovementioned is straightforward and intuitive, it has not been successfully implemented until two recent enabling technologies were made in registering and measuring nanonmeter (nm) deformations in response to nanoNewton (nN) forces (e.g., cell adhesion). WiMTiP is a technology that allows synthesizing a wrinkle free (smooth) nanometer metallic thin film embedded in a polymer matrix, dielectric gel mixtures, other biocompatible materials (e.g., gel and collagen), and the like. Smoothness and its metallic composition make the film highly reflective, while the film's nanometer thickness and its embedment in polymer make it highly deformable and elastic under large strains (>100%), that is the film will remain smooth, contiguous, and reflective under large deformations. Although it is simple concept, synthesis of such a smooth thin film over a polymer in the past has been proven difficult, since the persistent interfacial instabilities between film and polymer substrate cause wrinkles to form. These wrinkles have tens of microns (5~20 µm) in lateral spacing and submicron (~500 nm) roughness in height renders the film diffusive to visible light (i.e., the film ceases to be a mirror). A very reliable technique has been developed to suppress the instability that allows smooth thin films (e.g., WiMTiPs) to be synthesized. A sample PDMS-Al WiMTiP schematic shown in FIG. 5A. FIG. 5A shows a 20 µm PDMS layer 502, a 50 nm Al layer 504, a 1 mm PDMS layer 506, and a 1 mm glass substrate 508. The 50 nm Al layer 504 is positioned between the 20 µm PDMS layer 502 and the 1 mm PDMS layer 506, while the 1 mm glass substrate 508 is positioned below the 1 mm PDMS layer 506. Micrograph of the WiMTiP demonstrated its inherited elasticity under large strains, while nano-indentation experiments by atomic force microscopy (AFM) on WiMTiP and PDMS samples of the same thickness showed a surprising transition from viscoelasticity of PDMS (right curve FIG. 5B) to elasticity of a hard surface (left line FIG. 5B). It should be noted that merely 100 nN is needed to cause a 500 nm indentation, which provides the sensitivity needed to detect cell induced wall deformation for CTC enumeration and characterization.

Figure 6:
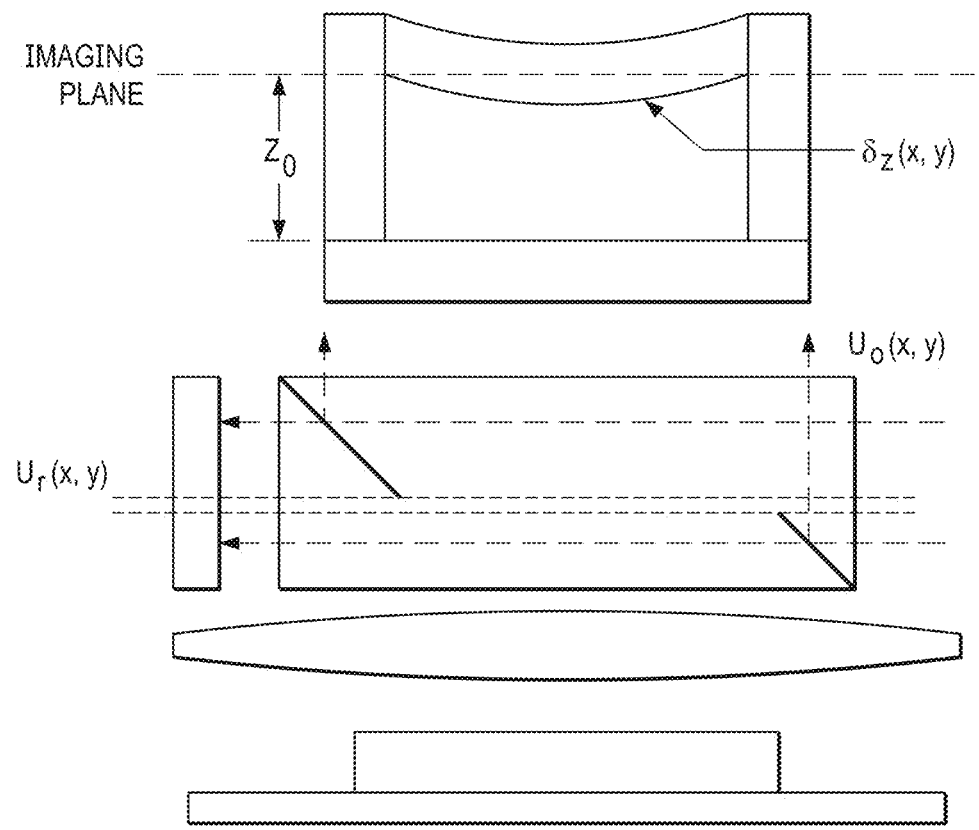
FIG. 6 illustrates measuring principle graphically according to aspects of the present disclosure.

DHMI (schematic in FIG. 4 and measuring principle graphically depicted in FIG. 6) measures CTC-induced nm-scale deformations that is "labeled" by the WiMTiP film as its deviation from the resting position, $\delta_z(x, y)$. To measure this strain, an object beam, $U_o(x, y)=A_o \exp[j2kn_p(z_0+\delta_z)]$, that illuminates the thin-film mirror and a reference beam, $U_r(x, y)=A_r \exp(j2kn_p z_0)$ interfere to obtain, $I(x, y)=A_o^2+A_r^2+2A_o A_r \cos[j2n_p k\delta_z(x,y)]$, where $n_p$ is the index fraction of the polymer and k is the wave vector. It thus concluded that $\delta_z$ is encoded as the spacing between any two adjacent fringes. A prototype of the microfluidics was developed and a portion of the interferogram was recorded by DHMI. It should be noted that interferences of the microfluidic channel at the beginning of the constriction by a WiMTiP film is clearly obtained.

Disclosed herein is the processing potential of a WiMTiP-DHMI device in performing CTC analysis on whole blood. Briefly, one milliliter of a patient's whole blood typically contains $5\times10^9$ erythrocytes, $7\times10^6$ leukocytes, $3\times10^8$ platelets, and 1~10 CTCs. The size of erythrocytes, leukocytes, platelets and CTCs is about 8 µm, 10-12 µm, 2-3 µm, and >15 µm (most are substantially larger), respectively. CTCs are highly deformable with wide range of elasticity, E, for example, less than 1 kPa.

Figure 5B:
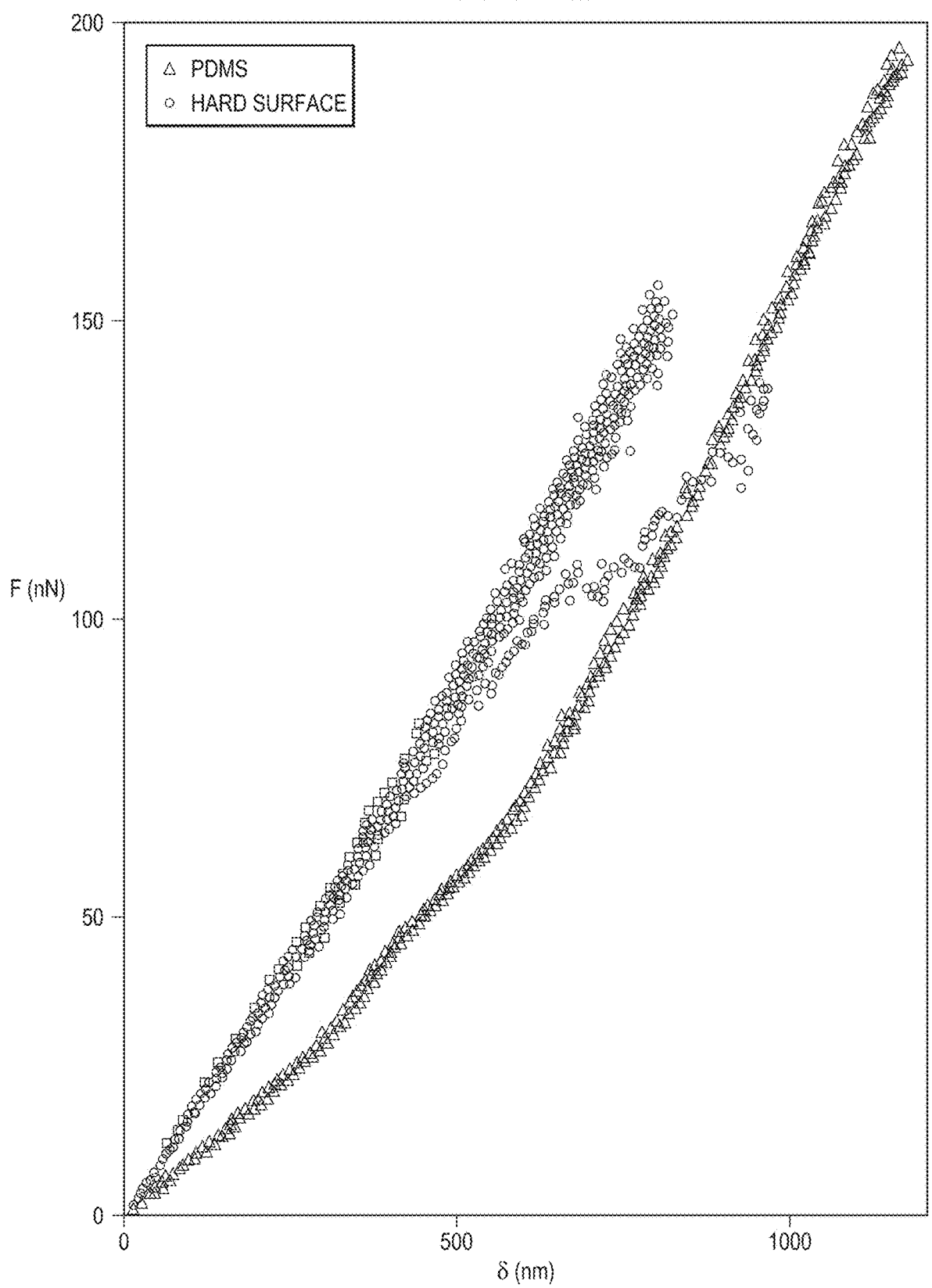
FIG. 5B illustrates nano-indentation experiments by atomic force microscopy (AFM) on a WiMTiP and PDMS sample of the same thickness of FIG. 5A.

As discussed above, the whole sample including CTCs and other hemocytes are pumped through a straight microchannel with a constriction section where a single WiMTiP film (e.g., 15 mm×40 mm) is located. The constriction section has a cross-section of 2 mm×15 µm in comparison to that of the main channel (2 mm×200 µm). As the cell passing through the constricted channel, only CTCs will deform appreciably and hence cause detectable deformation on the WiMTiP film. The high speed DHMI system operated at 10× magnification images up to 2 mm×2 mm WiMTiP area (or a sample volume of 2 mm×2 mm×15 µm per interferogram) at a lateral resolution of 0.7 µm, a deformation resolution of 10 nm (or equivalent to 1.5 nN for PDMS WiMTiP; FIG. 5B) and an acquisition rate of 2000 interferograms (or volume) per second. The maximum volume processed with the WiMTiP+DHMI platform is therefore 2 mm×2 mm×15 µm×2000 volumes/sec=0.12 mL/sec=7.2 mL/min.

The WiMTiP-DHMI platform is sensitive to detect nanometer deformation and associated forces. Measured by an AFM, the PDMS WiMTiP film (i.e., a PDMS-Al-PDMS composite; FIG. 5A) has a Young's modulus of 455.15±35 kPa in comparison to that of 329.64±10.65 kPa and exhibits clear linear force (F)—indentation (δ) relationship (right curve FIG. 5B) at a sensitivity of F/δ=~0.15 nN/nm. The sensitivity of the WiMTiP sensor is fine-tuned by selecting encasing polymer with bulk elasticity. Anecdotally, a gelatin WiMTiP achieving E=1.1 kPa has synthesized, similar to that of a breast cancer cell or a sensitivity of 0.5 pN/nm. It should be noted that the adhesion force (e.g., ~1 nN in REF) by a cancer cell would generate 1000 nm indent in such a WiMTiP sensor.

It is straightforward to expect the WiMTiP+DHMI platforms to obtain CTC cell size information simultaneously, since a cell leaves an equivalent or larger "footprint" (deformation) on a WiMTiP substrate than its original. Using the lateral dimension of the "footprint" allows for the approximation of the cell size information through modeling.

To scan 10 mL of whole blood in ~12 min, it requires recording and analyzing a total of 1.44 M interferograms. Reconstruction of two-dimensional (2D) deformation profiles of a WiMTiP film is computationally and data intensive. Fortunately, only those containing CTCs need to be analyzed, and that substantially reduces the data to a few hundred, a compression ratio of greater than 5000:1. With GPU processing development, 300 interferograms can be analyzed in 100 seconds or less.

Combining the above estimates of sample injection time (11 min), and data processing (~2 mins), indicates that the present system and methods can deliver results in about 13 minutes. Such incredible throughput is unmatched by current CTC technologies and have a significant impact on cancer research.

In an embodiment, the microfluidic device disclosed herein can detect, enumerate and characterize mechanical properties including size and stiffness of CTCs in whole blood by measuring directly nanoscale deformation on a novel thin film sensor (WiMTiP) and a DHMI when CTCs are forced through an instrumented narrow passage. Furthermore, the WiMTiP-DHMI platform is sensitive enough to differentiate CTC phenotypes. To this end, the present disclosure utilizes WiMTiP-DHMI microfluidics for high throughput enumeration and characterization of CTCs in whole blood and cross-platform validation of WiMTiP-DHMI technology and applications to phenotyping CTCs through membrane stiffness.

Current techniques for CTCs enumeration have low throughput, are inaccurate, laborious, and destructive to samples that requires additional downstream analyses to characterize the captured CTCs. As such, a high throughput CTC enumeration and characterization technology that is label free, non-destructive as disclosed herein is applicable to many cancers.

In some embodiments, a WiMTiP+DHMI apparatus (schematic shown in FIG. 4) includes a WiMTiP microfluidic and a DHMI. The WiMTiP microfluidic device includes a top-half straight glass channel (2 mm in width and 200 μm in height) wet etched by HF over a microscopic slide. Two fluids port are pre-drilled. The channel height in the middle is reduced to ~15 μm. A polymer (e.g., PDMS in FIG. 5A) thin layer containing a 50 nm wrinkle free Al film (WiMTiP) is first synthesized over a glass slide and then covalently bonded with the top half channel to form the WiMTiP microfluidics. The DHMI system includes a laser (e.g., 25 mW He—Ne, Newport Optics), beam collimating assembly (e.g., Thorlabs), a 40 mm 50:50 beamsplitter (e.g., Edmund Optics), a 75 mm dielectric mirror (e.g., Newport), macro projection lens (e.g., a Nikkor 105, Nikon), and an in-house assembled infinity corrected microscope using, for example, Nikon objectives and optics. The DHMI utilizes software to compute 3D deformation profiles from a DHMI recording. A platform with a PDMS-Al WiMTiP, in some embodiments, is used to obtain the WiMTiP deformation caused by passing leukemia (Jurkat) cells (FIG. 4), as well as to measure stresses generated by a live *Pseudomonas aeruginosa* (PA01) biofilm.

Furthermore, the WiMTiP and DHMI system is optimized to achieve more accurate enumeration and stiffness characterization of CTCs. Improvement of WiMTiP sensitivity that enables accurate detection and CTC "phenotyping" by CTC stiffness has been developed. Although capable of detecting a leukemia cell (FIG. 4), in some instances, PDMS-WiMTiPs can be too stiff (E=~400 kPa) in comparison to a CTC (E<1 kPa), leading to a small cell induced deformation on WiMTiP censor (~100 nm in FIG. 4). Since WiMTiP synthesis is not material specific, to improve the sensitivity, selection of polymers dielectric gel mixtures, other biocompatible materials (e.g., gel and collagen), and the like, with comparable E are used to improve sensitivity. Conventional biocompatible include, for example, gelatin, collagen and mixtures of PDMS and hydrogel at various mixing ratios. A gelatin-WiMTiP, whose sensitivity improves to 0.5 pN/nm from 150 pN/nm and reduces E=~1.1 kPa has been developed.

Other polymer composite, especially using mixture of gelatin, hydro gels, dielectric gel mixtures, and the like produce a much softer bulk substrate for metallic thin film sensors. Additionally, ferromagnetic nanoparticles and gel mixture are developed with the intention to provide dynamic tuning ability to WiMTiP sensor, that is the impedance of the sensor can be actively tuned as the CTC cell passes by providing additional cell detection modality.

Furthermore, addition of a digital holographic microscopy (DHM) in the platform provides another independent detection and provides additional information on cell membrane based on 3D Mie scattering of each individual cell. To establish mechanistic understanding of cell membrane mechanics to metastatic state and cancer type, both AFM and WiMTiP are utilized using both benign and malignant MB231 cells.

Using biological AFM and four cancer cell lines—prostate (PC3, LNCaP) and breast cancer (MCF-7, MB231) maintained and cultured, membrane properties including stiffness and elasticity are characterized to establish a database to determine the proper range of CTC stiffness and validate that membrane stiffness can distinguish CTC among each other and from other hemocytes. For comparison, stiffness of other hemocytes (neutrophils, monocytes, etc.) are also measured. Suitable polymers to improve WiMTiP sensitivity, WiMTiPs using gelatin, collagen, and PDMS-hydrogel mixtures can be synthesized based on these results. Stiffness of WiMTiPs are also characterized by AFM to identify suitable and sensitive WiMTiP and are integrated with existing DHMI.

In particular embodiments, four cancer cell lines have been utilized in the present disclosure. The buffer was seeded with two known concentrations (100 and 5000 per mL). These two cases emulate scenarios of a single or multiple CTCs passing over a WiMTiP sensor, respectively. The suspension is injected into the WiMTiP microchannel at constant flow rate and holographic interferograms is recorded using DHMI under flow rates (1, 10, and 20 mL/min). The 3D deformation profiles of WiMTiP as cells passing by were reconstructed from interferograms and averaged to establish a DHMI deformation database for each cancer cells and develop a cross-correlation algorithm to provide a detection confidence and to mitigate false positives for detection and classification was established.

In particular embodiments, four cancer cell lines have been utilized in the present disclosure. A known number of tumor cells (0, 100, 1000, 2000, and 5000 per mL of blood) were spiked into healthy human blood diluted with saline at various concentrations (1:10, 1:5, and 1:1) to understand influence of background hemocytes on CTC WiMTiP signature. Since most hemocytes are smaller than the constriction, the imprint is expected to resemble background noise. A parameter of quality measurement defined as the correlation coefficient of the identified deformation with the database divided by the mean power of the noise (or standard deviation of background deformation) was used to mitigate the identification of false positives.

In some instances, limitation of the WiMTiP-DHMI is that background noise originated from flow pressure, shear stress, high concentration blood cells may overwhelm CTC-induced WiMTiP deformation. The noise is reduced by reducing sample injection speed and diluting sample concentration. Additionally, a supported vector machine (SVM) classifier trained on previous datasets established in the previous experiments, was constructed to improve detection accuracy under noise and characterization.

Currently no gold-standard technology exists for CTC isolation. Commercial antibody-based methods (e.g., CELLSEARCH® CTC Kit or CELLSIEVE™ CTC Enumeration Kit) are chosen, allowing the comparison of results with a large body of work. This task helps in fine-tuning the criteria and control parameters for identifying CTCs using WiMTiP-DHMI.

To benchmark the method for enumerating cancer cells in the whole blood, commercially available CTC enumeration kit (e.g., CELLSEARCH® CTC Kit or CELLSIEVE™ CTC Kit) are utilized. Healthy whole blood was seeded with four cancer cell lines (PC3, LNCaP, MCF-7, MB231, and their combinations) at concentrations (1, 10, 100, and 1000 cells/mL) and cultured. WiMTiP-DHMI systems were validated with concurrent experiments using commercial CTC kit and epi-fluorescence microscopy to correlate the two approaches.

To develop insights into the potentials to differentiate CTC types or potentially detecting cancer progression based on mechanical properties of cancer cells, commonly accepted procedures are utilized. Using a membrane characteristic database measured by AFM and buffer suspensions of four cancer cell lines, as well as their combinatorial mixture, WiMTiP-DHMI platforms are used to measure cell-induced wall deformation and subsequently inferring its mechanical properties. Apart from static (time-averaged) property (stiffness), dynamic property (e.g., viscoelasticity) of a cell will be focused on. During each experiment, as cancer cells passing through a WiMTiP channel, oscillatory hydrodynamic perturbations by simply coupling an inline peristaltic pump were introduced into the mean flow to cause the cell to accelerate and decelerate periodically (i.e., to provide a cyclic loading and unloading). The evolution of cell-induced WiMTiP deformation was recorded by high-speed camera (e.g., 2 kHz). The frequency relationship between the deformation and perturbation provided an estimation of cancer cell viscoelasticity (or "fluidity"). A database on the viscoelasticity of each cancer cell line was established for potential mechanical "phenotyping".

However, in some instances where tumor cell counts from the commercial kits do not quantitatively match that from WiMTiP-DHMI, experiments with increasing number of spiked cells that show a consistent offset between the two approaches can be "calibrated" the methods as needed.

There are over 100 CTC enumeration technologies currently being explored. In this growing ecosystem of innovative CTC technologies, the present disclosure seeks to develop a new technology for enumerating and characterize CTCs based on mechanical properties, which would supersede prior approaches in the following: (1) The Applicability to metastatic and non-metastatic Cancers: The systems and methods disclosed herein to enumerate CTCs is based on simultaneously measuring multiple biophysical properties of cancer cells. Such a label-free approach makes it applicable to CTC detection in all cancers; (2) The robust CTC counts: In comparison to existing slow processing speed at typically 1 mL/hour, the systems and methods disclosed herein offer significant throughput (10 mL/min) and robust CTC counts; and (3) Phenotyping the Heterogeneity in CTCs with Multiple Biophysical Properties: The approach disclosed herein is culture-free and provides multiple readouts resolving significantly the heterogeneity in CTCs. The multiple biophysical "fingerprinting" and subsequent classification enable phenotyping CTCs in its natural complexity.

As demonstrated herein, the systems and methods of the present disclosure provide a low-cost, scalable WiMTiP technology for measurement of CTC deformation over a substrate that allows the registration of pressure as nanometer substrate deformation (e.g., PDMS-WiMTiP). Furthermore, digital holographic interferometry is shown to optically and non-invasively "decode" the deformation registered by WiMTiP passive sensor at the sensitivity of <10 nm deformation. The sensitivity of the PDMS-WiMTiP sensor has been confirmed by an experiment using agar gel. A thin layer of agar gel was coated on WiMTiP sensor. The dehydration and rehydration of the coated gel film exerted interfacial stresses over the nano-sensor, which was used to estimate how PDMS-WiMTiP CTC sensor measure the wall stress at the accuracy of <1 pN or equivalently detect cells with their membrane elastic modulus of ~1 kPa.

As demonstrated herein, a bench-top WiMTiP-DHMI system has been established and a new WiMTiP-DHMI sensor with improved sensitivity with newly developed impedance-matched WiMTiP-metamaterial has been developed. The bench-top system (i.e., WiMTiP-DHMI or WIM-TIP-DHMI) includes a WiMTiP microfluidic sensor that registers nanoscale strain deformation over the sensor as CTC cells pass over it and a DHMI subsystem non-intrusively measures the nano-strain.

Additionally, a new impedance matching WiMTiP sensor has been developed along with the associated microfabrication procedures. The new WiMTiP sensor is made of softer hybrid polymers (e.g., PDMS and hydrogel), which reduces Young's modulus of 300 kPa to 10 kPa which matches the membrane elasticity of most cancer cells. Data analysis methodologies to measure and characterize nano imprints by various passing CTCs have also been developed. In some embodiments, the analysis methodology includes recording and enhancing digital holographic interferograms, phase integrations, and finally nano-deformation of nano-strain WiMTiP sensors. The analysis software has been validated, and additionally, parallel processing code has also been implemented in high-performance cluster (HPC) computing systems to improve the performance and analysis throughput. Realistic rheological membrane models have been developed using AFM measurements. A multi-power-law viscoelastic membrane model based on Ting's integral has been developed that allows quantification of cell viscoelasticity directly and later provides that ability to distinguish cells from different sites based on membrane material properties. This particular model has been validated against three cancer cell lines. Additional models utilizing additional cancer cell lines (e.g., PC3, LNCaP, MCF7, MB231) are feasible. Established cancer cell line cultures include colon cancer (PC3, LNCap), breast cancer (MCF-7, MB231, T47D), and lung (A45C, A549), with additional cell lines feasible. AFM methodologies to quantify and characterize rheological property of live CTC cells have been developed and viscoelastic measurements of various proposed cell sites has also been completed. In some embodiments, the AFM-based methodology includes custom-made flow cells allowing simultaneous cell observation and nano-indentation measurement as well as data analysis based on Ting's integral model. Results show that site discrimination can be found in viscoelastic behavior of cancer cells.

An embodiment provides WiMTiP-DHMI microfluidic technology that enables high throughput, non-destructive, in vitro detection, enumeration, and mechanical characterization of CTC cells in whole blood samples. This is enabled by wrinkle free metallic nanometer (>50 nm) thin film in polymer nanostrain technology as disclosed herein. Differing from both existing immunogenic capturing and label-free detection techniques, the systems and methods disclosed herein detect and simultaneously characterize CTCs in whole blood without cumbersome, time consuming, and destructive preparation procedures. The WiMTiP-DHMI microfluidic technology achieves CTC detection and characterization by measuring cell induced nanometer deformation in a compliant wall as blood sample passes through a constricted microchannel with a cross-sectional dimension close to that of a CTC. The nanometer deformation captured by the WiMTiP nanostrain sensor embedded in the compliant wall is remotely measured by a digital holographic microscopic interferometer capable of resolving 10 pN.

A further embodiment provides a WiMTiP-DHMI system including a microfluidic channel embedded with a WiMTiP nanostrain sensor and a DHMI. The associated data acquisition and analysis algorithms focus on strain response of the WiMTiP to various cell suspensions, including CTCs and other blood cells with different cell compositions and concentrations. Time series of instantaneous nanostrain fields captured by the WiMTiP-DHMI system and concurrently time-resolved microscopic images of the cells at the same measurement area provide visual validation for cell detection and identification.

In an embodiment, the WiMTiP-DHMI system includes a microfluidic channel with three constriction geometry (15, 20, and 30 μm in depth) with an Al-PDMS-WiMTiP sensor and a digital holographic microscopic interferometer. In some embodiments, the constricted section of the microfluidic channel has a depth in a range between 15 μm to 30 μm. The microfluidics is composed of two glass walls. One wall contains an etched microchannel and the other wall has the WiMTiP composite coating with a 50 nm thin film mirror. A reflective DHMI is composed of a laser and beam shaping optics as well as a reflective Mach-Zehnder interferrometer including a beamsplitter, mirror in reference beam, thin film mirrors in WiMTiP sensors, and a high-speed camera with an imaging lens whose imaging plane is located at the resting plane of the micro-mirror in WiMTiP. The "mirror" nanometer deformations in the WiMTiP are registered as its deviation in the depth direction from its rest position. The deviation is encoded as a phase change in the object beam. The reflected object beam, combined with the reference beam, forms the interference pattern. The phase information recorded is then recovered digitally by an algorithm In an embodiment, data analysis software decodes nanoscale deformation of the WiMTiP sensor. The decoding software has also been implemented in parallel scheme to improve its throughput. Validation experiments on 20 μm inert particles in a dense 2 μm particle suspension have been conducted showing successful detection and enumeration of 20 μm particles. Validation experiments on PC3 and MCF-7 in Dulbecco's phosphate-buffered saline (DPBS) suspension have also been performed. The detection of the passing PC3 and MCF-7 has been achieved. Clear differences in imprints between PC3 and MCF-7 are observed.

Additionally, methodologies and analysis algorithms relating CTC stiffness to instantaneous WiMTiP nanostrain fields utilizing mechanistic models describing interactions of WiMTiP sensors, CTCs, and background fluids (e.g., plasma, red blood cells, white blood cells, etc.) under various flow conditions are feasible. For example, in some embodiments, membrane stiffness of four cancer cell lines such as prostate (PC3, LNCaP) and breast cancer (MCF-7, MB231) and other hemocytes models are established by performing nano-indentation experiments. In this example, a correlation model relating WiMTiP deformation measurement to types of blood cells passing by are used for CTC identification and approximation of CTC mechanical properties under flow conditions. This enables "phenotyping" CTCs origins and metastatic states via their membrane stiffness.

A "wet" AFM based nano-indentation technique has been developed to establish ground cancer cell membrane rheology mechanics, which is used in the development of WiMTiP-cell interaction models. These techniques allow direct quantification of the membrane viscoelasticity of live cancer cells in realistic environments. Briefly, before each measurement, cultured cancer cells are "plated" onto an 8 mm circular glass slide. The "plated" slide is then placed in an in-house developed flow cell with a "mirror" bottom and filled with DPBS or culture medium. Nano-indentation experiments are then performed in an atomic force microscope using a submersible probe holder equipped with an 20X extra-long working distance microscope (200 mm). This setup allows the observation of cell morphology and the ability to perform nano-indentation measurements simultaneously. Data analysis algorithms using a multi-power-law viscoelasticity model based on Ting's integral method has been developed using nonlinear global optimization and validated on PDMS and PDMS-metal composites. Validation results show that measurement accuracy of elasticity and viscoelasticity model are within <3% of published results. The measurement and analysis systems have been applied to PC3 and MCF-7 cell lines. Measurements of Young's modules were obtained and consistent with published results within 5% margin of errors. Viscoelasticity analysis on PC3 and MCF-7 cell lines are feasible. Results support the hypothesis that viscoelasticity model parameters clearly show differentiation between cancer types. A finite-element model of WiMTiP-cell interactions are feasible.

Optimization of WiMTiP-DHMI systems to achieve real-time CTC cell detection and enumeration in whole blood samples and to improve WiMTiP sensor sensitivity for cell phenotyping is disclosed herein. Although measuring CTC membrane properties are computation intensive, real-time detection and enumeration of CTC in whole blood is feasible. Guidelines and prototypes that lead to a point-of-care device are established by optimization (e.g., flow rate of blood sample, WiMTiP sensor size and composition, detector acquisition rate, microchannel geometry, and their calibrations). Additionally, new WiMTiPs with high stress-strain sensitivity (e.g., ~1 pN/nm) by synthesizing WiMTiP in other soft elastomers including gelatin, collagen, and PDMS-hydrogel mixtures are optimized to select optimal polymers that matches resonant frequencies to CTC elasticity.

For example, as disclosed herein, advancements in WiMTiP sensor material technology have been achieved. New WiMTiP sensors using impedance matching polymer materials have been developed. In some embodiments, the new sensor material is composed of a mixture of PDMS (SYLGARD™ 184) and a dielectric gel (SYLGARD™ 527). It was found using AFM nano-indentation, a fractional mixture of PDMS and SYLGARD™ 527 at a volume ratio of 1:10 yields the Young's modulus at 2 kPa, which is about 2 to 3 time larger than most cancer cells. A new WiMTiP sensor made of this softer polymer mixture as the bulk material has been successfully fabricated. It has been found that original microfabrication process using Perylene-C as interfacial jammer ceases to function when material interfacial elasticity below 50 kPa. A modified protocol based on poly electrolyte multi-layer (PEM) technology has been successfully developed and used to fabricate a new WiMTiP sensor with bulk elasticity of 2 kPa. The sensor has been applied to PC3 and MCF-7. Studies show that as 25 μm PC3 and 20 μm MCF-7 pass through a 15 μm WiMTiP-microfluidic restriction, a strong strain deformation of 400 nm and 210 nm is observed in comparison to those of 35 nm and 24 nm, respectively. In short, a highly sensitive WiMTiP sensor has been developed and demonstrates the system's feasibility to identify various cancer types. Additional biocompatible materials including, for example, gelatin and collagen are also suitable materials. Furthermore, optimization of setup and data analysis software have been completed. For instance, the optimization of the system setup includes addition of a high-quality macro imaging lens as a projection lens in the DHMI system and replacement of a high-speed large format complementary metal oxide semiconductor (CMOS) camera to improve throughput. Additionally, implementation of both parallel and graphic processing units (GPUs) for computation analysis expedites DHMI processing speed by 7-fold.

Sensor material optimization using additional materials (e.g., gelatin or collagen) is possible. For instance, better performance than current PDMS and dialectic gel composites is achieved with material optimization. This is evident by detection and characterization capability against various cell lines in PBS.

A further objective of the present disclosure relates to cross-platform validation of WiMTiP-DHMI microfluidic technology and its application to phenotyping CTCs through membrane stiffness. The use of whole blood samples spiked with four CTC cell lines (prostate: PC3, LNCaP; and breast cancer: MCF-7, MB231) and the optimized bench-top system, validate the accuracy of detection and enumeration and demonstrate the system's efficacy. The systems and methods of the present disclosure are readily applied to various suspensions to demonstrate their detection efficacy and accuracy. Some nonlimiting examples of suspensions at various controlled concentration include inert particles in buffer, four CTC cell lines spiked in buffer, and CTCs in whole blood. These results are cross-validated with commercial CTC enumeration kits and flow cytometry.

For example, multiple cell lines cultures including prostate (PC3 and LNCap), breast cancer (MCF-7 and MB231), as well as additional cell lines such as breast cancer (T47D, 4T1, and MDA-MB-231), lung cancer (A549 and H358) have been established. Accuracy and efficacy studies using WiMTiP-DHMI systems using Al-PDMS-WiMTiP sensors on inert particles and two cancer cell lines in buffer solution have been conducted. Successful detection and enumerations of both inert particles and spiked cancer cell lines (PC3 and MCF-7) have been achieved. Results have been confirmed with concurrent optical microscopic observations.

Furthermore, results show a detection rate of 100%, 91%, and 80% for inert latex beads, PC3, and MCF-7, respectively. MCF-7 show the lowest detection rate as MCF-7s are substantially soft. Accuracy and efficacy studies using optimized WiMTiP sensor on inert particles, PC3, and MCF-7 have also been performed. Owing to improved strain sensitivity of the sensor from 1 nN/nm to 10 pN/nm, substantial improvement on sensor responses and detection accuracies was observed. Analysis based on various experiments show that the detection rates achieve 100%, 99%, and 97% for inert particles, PC3, and MCF-7 in suspension, respectively. These results demonstrate the feasibility of the WiMTiP-DHMI technology for CTC cell detection, enumeration, and characterization.

High accuracy and efficacy results have been obtained using PC3 and MCF-7 cell lines. As such, high accuracy and efficacy using cells in whole blood are feasible. For example, in some embodiments, concentrations of cancer cells (e.g., PC3 and MCF-7) and concentrations of blood (e.g., blood: PBS ratios of 1:10, 1:5, 1:1, 5:1, 10:1, and 100:0) of a sample can be systematically varied and processed through the WiMTiP-DHMI platforms, including optimized WiMTiP sensors, for detection of CTCs, enumeration of CTCs in the sample, characterization of biophysical properties, CTC cell size, CTC cell membrane deformability, stresses on CTC cell membranes, adhesion stress on CTC cells, normal stress of CTC cells, and the like. As previously discussed, utilization of other cancer cells, such as LNCap, MB231, T47D, and 4T1 are feasible.

Studies on multi-modal CTC characterization and potential "phenotyping" using both static (stiffness/elasticity) and dynamic membrane characteristics (viscoelasticity) by WiMTiP-DHMI have been conducted. A comparative study using four cancer cell lines, one healthy prostate cell line, and solid particles in buffer is conducted by flowing the suspensions through microfluidics at constant speed (static) and at oscillatory flows with a mean (dynamic). The membrane properties (e.g., stiffness/elasticity and viscoelasticity) are measured and comprehensive databases on static and dynamic membrane characteristics are established to facilitate the development of new multi-modal CTC characterization methodology to phenotype CTCs and their malignant states.

Methodologies to establish mechanistic matrices (framework) to perform multi-modal CTC characterization based on dynamic membrane characteristics were developed. For instance, the method includes wet AFM technology capable of performing nano-indentation in live tissues in liquids, protocols for conducting nano-indentation experiments for both attached and suspended cancer cells, and a quantitative model matrix describing accurately static (elasticity) and dynamic (viscoelasticity) membrane characteristics based on nano-indentation measurements. Quantitative non-linear model using modified Legendre integral (or Ting's integral) have been developed and multi-power law membrane model characteristics were observed. This is the first time that model parameters estimated from nano-indentation experiments have been developed. Results on PC3 and MCF-7 suggest that the model is sufficiently sensitive to phenotype cancer type. Construction of multi-modal cancer characterization databases and frameworks that allows the "phenotyping" of different cancer types is feasible. Measurements on PC3, MCF-7, and T47D have been completed, while analysis on PC3 and MCF-7 have been accomplished. Development of artificial intelligence (AI)-based phenotype classifying based on deep learning methods are in progress. Simple, but robust, flow control technique allowing WiMTiP-DHMI measurement under both steady and oscillatory flow conditions have been developed. Additionally, benign and malignant MB231 cell lines have been established, and membrane characterization and WiMTiP measurements are feasible.

Moreover, other polymer composites (e.g., mixtures of gelatin, hydrogels, dielectric gels, etc.) to achieve much softer bulk substrate for metallic thin film sensor have been explored. Additionally, ferromagnetic nanoparticles and gel mixture developments to provide dynamic tuning ability to WiMTiP sensor (i.e., the impedance of the sensor to be actively tuned as the CTC cell passes by) have been initiated. To provide additional cell detection modality, a digital holographic microscopy has been added to the systems and platforms of the present disclosure. Concurrent digital holographic microscopy observations provide another independent detection means and provides additional information on cell membrane based on 3D Mie scattering of each individual cell. To establish mechanistic understanding of cell membrane mechanics to metastatic state and cancer type, both AFM and WiMTiP systems have been developed using both benign and malignant MB231 cells. The results from these systems provide insight leading to relevant cancer cell membrane model development.

The above systems and methods are further applicable to LNCap, MB231, T47D, 4T1, and A549 cell lines. The viscoelasticity of these cancer cells is measured by nano-indentation and quantified by multi-power-law membrane models. These measurements provide vector machine classification criteria. The data is also utilized in multi-modal databases to facilitate the high-fidelity detection, enumeration, and characterization of various CTC cells. The framework is then applied to benign and malignant MB231 cells to validate that viscoelasticity of cell membranes change based on its metastatic state and the WiMTiP-DHMI systems presented herein, and are sensitive enough to detect subtle differences. In addition, improvement to WiMTiP-DHMI system sensitivity by imposing dynamic loading on cell membrane with oscillatory flow is feasible.

In view of the aforementioned, in an embodiment, the present disclosure pertains to a method of performing circulating tumor cell (CTC) analysis. In general, the method includes flowing a sample through a CTC microfluidic platform, deforming a CTC within the sample, measuring CTC deformation through an imprint of the deformed CTC, processing data related to the measuring, and at least one of identifying or characterizing parameters related to the data that enables at least one of detection of CTCs, enumeration of CTCs in the sample, characterization of biophysical properties, CTC cell size, CTC cell membrane deformability, stresses on CTC cell membranes, adhesion stress on CTC cells, normal stress of CTC cells, or combinations thereof. In some embodiments, the flowing includes passing the sample through a channel of the CTC microfluidic platform having a constricted section.

In some embodiments, the at least one of identifying or characterizing occurs without destruction or modification to the sample. In some embodiments, the sample includes blood. In some embodiments, the CTC analysis is performed during a time period in a range of 1 to 15 minutes. In some embodiments, the CTC analysis is performed in 13 minutes or less.

In some embodiments, the CTC microfluidic platform includes an inlet and an outlet formed on the channel and a nanostrain sensor between the inlet and the outlet and operable to contact the sample flowing through the channel. In some embodiments, the nanostrain sensor includes a first layer, a metallic layer, a second layer, and a substrate. In some embodiments, the CTC microfluidic platform includes a reflective digital holographic microscopic interferometry (DHMI) system.

In some embodiments, the first layer and the second layer can each independently include, without limitation, polydimethylsiloxane (PDMS), a polymer, gelatin, collagen, mixtures of PDMS, and combinations thereof. In some embodiments, the first layer and the second layer include PDMS.

In some embodiments, the metallic layer is a layer includes a metal that can include, without limitation, alkaline metals, alkaline earth metals, transition metals, metalloids, and combinations thereof. In some embodiments, the metallic layer can include, without limitation, Al, Au, Zn, Ag, Cr, and combinations thereof.

In some embodiments, the substrate includes an optically transparent substrate. In some embodiments, the optically transparent substrate is glass.

In some embodiments, the channel includes a midsection, an inlet section, and an outlet section. In some embodiments, the midsection is longer than an overall length of the channel, and the midsection includes a smaller channel height relative to at least one of a height of the inlet section or a height of the outlet section.

In some embodiments, the nanostrain sensor includes a wrinkle-free metallic thin film in polymer (WiMTiP). In some embodiments, the WiMTiP has no residual stress, is optically smooth (specular reflectivity), and electrically conductive.

In some embodiments, the measuring includes detecting deformation via the nanostrain sensor utilizing the reflective DHMI system. In some embodiments, three-dimensional (3D) deformation profiles of the nanostrain sensor as cells passing by the nanostrain sensor are reconstructed from interferograms from the reflective DHMI system. In some embodiments, the reflective DHMI system includes laser and beam shaping optics and a reflective Mach-Zehnder interferometer having of a beam splitter, a mirror in reference beam, and a recording camera. In some embodiments, the nanostrain sensor includes a wall mounted WiMTiP nanostrain sensor.

In some embodiments, the method further includes creating a biophysical fingerprint and phenotyping the CTC based, at least in part, on the fingerprint.

In an additional embodiment, the present disclosure pertains to a microfluidic platform. In some embodiments, the microfluidic platform includes a channel having an inlet and an outlet, a nanostrain sensor between the inlet and the outlet and operable to contact a sample flowing through the channel. In some embodiments, the nanostrain includes a first layer, a metallic layer, a second layer, and a substrate. In some embodiments, the microfluidic platform further includes a digital holographic microscopic interferometry (DHMI) system.

In some embodiments, the first layer and the second layer can each include, without limitation, polydimethylsiloxane (PDMS), a polymer, gelatin, collagen, mixtures of PDMS, and combinations thereof. In some embodiments, the first layer and the second layer include PDMS. In some embodiments, the metallic layer is a layer includes a metal that can be, without limitation, alkaline metals, alkaline earth metals, transition metals, metalloids, and combinations thereof. In some embodiments, the metallic layer includes Al, Au, Zn, Ag, Cr, and combinations thereof. In some embodiments, the substrate is glass. In some embodiments, the channel includes a midsection, an inlet section, and an outlet section. In some embodiments, the midsection is longer than an overall length of the channel and the midsection includes a smaller channel height relative to at least one of a height of the inlet section or a height of the outlet section. In some embodiments, the midsection is long and has a smaller channel height relative to at least one of a height of the inlet section or a height of the outlet section. In some embodiments, the nanostrain sensor includes a wrinkle-free metallic thin film in polymer (WiMTiP). In some embodiments, the WiMTiP has no residual stress, is optically smooth (specular reflectivity), and electrically conductive.

In an additional embodiment, the present disclosure pertains to a method of fabricating a microfluidic system. Generally, the method includes fabricating a top half, synthesizing layer-by-layer a bottom half of the microfluidics containing WiMTiP nanostrain sensor, and integrating the top half and the bottom half. In some embodiments, the top half fabrication includes creating a mask of top-half microchannel, patterning the mask over an optically transparent substrate (e.g., glass, optical windows, etc.), wet-etching the patterned substrate by alternatively etching by HF and HCl until each portion of the channel reaches its designated height, and forming an inlet and an outlet port. In some embodiments the bottom half fabrication includes forming a mixture having an elastomer and a curing agent, depositing the mixture on the substrate and subsequently curing the mixture, depositing nano-particle (NP) jammer, depositing a metal film through a shadow mask showing the shape of the sensor on the substrate, and spincoating a second polymeric layer (i.e., a bottom half microfluidics with a WiMTiP sensor).

In some embodiments, the channel includes a long channel midsection relative to a length of the channel. In some embodiments, the mask is an SU8 mask. In some embodiments, the elastomer is a silicone elastomer (e.g., SYLGARD™ 184). In some embodiments, the cured mixture is polydimethylsiloxane (PDMS). In some embodiments, the metal film includes Al. In some embodiments, the method further includes depositing a jammer on the substrate. In some embodiments, the jammer includes Perylene-C. In some embodiments, the polymeric layer includes PDMS. In some embodiments, the method further includes, prior to the spincoating, depositing Perylene-C to prevent leaching of sensory materials in liquid. In some embodiments, the integration of the top half and the bottom half includes $O_2$-plasma activated bonding.

In a further embodiment, the present disclosure pertains to a method of performing circulating tumor cell (CTC) analysis. Generally, the method includes flowing a sample (e.g., blood) through a CTC microfluidic platform, deforming a CTC within the sample, measuring the CTC deformation through the imprint of a deforming CTC on a wall mounted nanostrain sensor, processing data related to the detection, and identifying parameters related to the data that enables, without limitation, detection of CTCs, enumeration of CTCs in the sample, and characterization of their biophysical properties: CTC cell size, CTC cell membrane deformability, stresses on CTC cell membranes, adhesion stress on CTC cells, normal stress of CTC cells, and combinations thereof. In some embodiments, the flowing includes passing the sample through a constricted section of the CTC microfluidic platform.

In some embodiments, the identifying and characterization occurs without destruction or modification to the sample (e.g., blood). In some embodiments, the CTC analysis is performed during a time period between 1 and 15 minutes. In some embodiments, the CTC analysis is performed in 13 minutes. In some embodiments, the CTC microfluidic platform includes a channel having an inlet and an outlet, a nanostrain sensor between the inlet and the outlet and operable to contact a sample flowing through the channel. In some embodiments, the nanostrain sensor includes a first layer, a metallic layer, second layer, and a substrate. In some embodiments, the CTC microfluidic platform includes a reflective digital holographic microscopic interferometry (DHMI) system. In some embodiments, the nanostrain sensor includes a wrinkle-free metallic thin film in polymer (WiMTiP). In some embodiments, the WiMTiP has no residual stress, is optically smooth (specular reflectivity), and electrically conductive. In some embodiments, the detecting includes measuring deformation via the nanostrain sensor utilizing the reflective DHMI system. In some embodiments, three-dimensional (3D) deformation profiles of the nanostrain sensor as cells passing by the nanostrain sensor are reconstructed from interferograms from the reflective DHMI system. In some embodiments, the method further includes creating a biophysical fingerprint and phenotyping the CTC based, at least in part, on the fingerprint. In some embodiments, the reflective DHMI system includes a laser and beam shaping optics as well as a reflective Mach-Zehnder interferometer having of a beam splitter, mirror in reference beam, wall mounted WiMTiP nanostrain sensor, and a recording camera.

Although various embodiments of the present disclosure have been illustrated in the accompanying Drawings and described in the foregoing Detailed Description, it will be understood that the present disclosure is not limited to the embodiments disclosed herein, but is capable of numerous rearrangements, modifications, and substitutions without departing from the spirit of the disclosure as set forth herein.

The term "substantially" is defined as largely but not necessarily wholly what is specified, as understood by a person of ordinary skill in the art. In any disclosed embodiment, the terms "substantially", "approximately", "generally", and "about" may be substituted with "within [a percentage] of" what is specified, where the percentage includes 0.1, 1, 5, and 10 percent.

The foregoing outlines features of several embodiments so that those skilled in the art may better understand the aspects of the disclosure. Those skilled in the art should appreciate that they may readily use the disclosure as a basis for designing or modifying other processes and structures for carrying out the same purposes and/or achieving the same advantages of the embodiments introduced herein. Those skilled in the art should also realize that such equivalent constructions do not depart from the spirit and scope of the disclosure, and that they may make various changes, substitutions, and alterations herein without departing from the spirit and scope of the disclosure. The scope of the invention should be determined only by the language of the claims that follow. The term "comprising" within the claims is intended to mean "including at least" such that the recited listing of elements in a claim are an open group. The terms "a", "an", and other singular terms are intended to include the plural forms thereof unless specifically excluded.

What is claimed is:

1. A method of performing circulating tumor cell (CTC) analysis, the method comprising:
    flowing a sample through a CTC microfluidic platform, wherein the flowing comprising passing the sample through at least one channel of the CTC microfluidic platform having a constricted section, wherein the CTC microfluidic platform comprises: an inlet and an outlet formed on the at least one channel; a nanostrain sensor between the inlet and the outlet and operable to contact the sample flowing through the at least one channel, the nanostrain sensor comprising: a first layer; a metallic layer; a second layer; and a substrate; and a reflective digital holographic microscopic interferometry (DHMI) system;
    deforming a CTC within the sample;
    measuring CTC deformation through an imprint of the deformed CTC;
    processing data related to the measuring; and
    at least one of identifying or characterizing parameters related to the data that enables at least one of detection of CTCs, enumeration of CTCs in the sample, characterization of biophysical properties, CTC cell size, CTC cell membrane deformability, stresses on CTC cell membranes, adhesion stress on CTC cells, normal stress of CTC cells, or combinations thereof.

2. The method of claim 1, wherein the at least one of identifying or characterizing occurs without destruction or modification to the sample.

3. The method of claim 1, wherein the sample selected from the group consisting of blood, prostate cells PC3 or LNCap, breast cancer cells MCF-7, MB231, T47D, 4T1, or MDA-MB-231, lung cancer cells A549 or H358, plasma, red blood cells, white blood cells, a phosphate buffered saline (PBS)-blood mixture, and combinations thereof.

4. The method of claim 1, wherein the constricted section has a depth in a range between 15 μm to 30 μm.

5. The method of claim 1, wherein the first layer and the second layer are each independently selected from the group consisting of polydimethylsiloxane (PDMS), a polymer, gelatin, collagen, mixtures of PDMS, hydrogel, a dielectric gel, an impedance matching polymer material, a PDMS-hydrogel mixture, a soft elastomer, a biocompatible material, a polymer that matches resonant frequencies to the CTC elasticity, and combinations thereof.

6. The method of claim 1, wherein the first layer comprises PDMS and the second layer comprises a dielectric gel.

7. The method of claim 6, wherein the PDMS and the dielectric gel have a volume ratio of 1:10 (PDMS:dielectric gel).

8. The method of claim 1, wherein the metallic layer is a layer comprising a metal selected from the group consisting of alkaline metals, alkaline earth metals, transition metals, metalloids, and combinations thereof.

9. The method of claim 1, wherein the metallic layer comprises a metal selected from the group consisting of Al, Au, Zn, Ag, Cr, and combinations thereof.

10. The method of claim 1, wherein the substrate comprises an optically transparent substrate.

11. The method of claim 10, wherein the optically transparent substrate is glass.

12. The method of claim 1, wherein the at least one channel comprises a midsection, an inlet section, and an outlet section.

13. The method of claim 12, wherein the midsection is longer than an overall length of the at least one channel, and wherein the midsection comprises a smaller height relative to at least one of a height of the inlet section or a height of the outlet section.

14. The method of claim 1, wherein the nanostrain sensor comprises a wrinkle-free metallic thin film in polymer (WiMTiP).

15. The method of claim 14, wherein the WiMTiP has no residual stress, is optically smooth (specular reflectivity), and electrically conductive.

16. The method of claim 1, wherein the measuring comprises detecting deformation via the nanostrain sensor utilizing the reflective DHMI system.

17. The method of claim 16, wherein three-dimensional (3D) deformation profiles of the nanostrain sensor as cells passing by the nanostrain sensor are reconstructed from interferograms from the reflective DHMI system.

18. The method of claim 1, wherein the reflective DHMI system comprises laser and beam shaping optics and a reflective Mach-Zehnder interferometer having of a beam splitter, a mirror in reference beam, and a recording camera; and wherein the nanostrain sensor comprises a wall mounted WiMTiP nanostrain sensor.

19. The method of claim 1, further comprising:
creating a biophysical fingerprint; and
phenotyping the CTC based, at least in part, on the fingerprint.

* * * * *